US010295507B2

(12) United States Patent
Dual et al.

(10) Patent No.: US 10,295,507 B2
(45) Date of Patent: May 21, 2019

(54) METHOD AND DEVICE FOR MULTIPLE-FREQUENCY TRACKING OF OSCILLATING SYSTEMS

(71) Applicant: ETH ZURICH, Zurich (CH)

(72) Inventors: Jurg Dual, Elsau (CH); Tobias Brack, Dübendorf (CH); Robin Vujanic, Zürich (CH)

(73) Assignee: ETH ZURICH, Zurich (CH)

( * ) Notice: Subject to any disclaimer, the term of this patent is extended or adjusted under 35 U.S.C. 154(b) by 236 days.

(21) Appl. No.: 15/302,824

(22) PCT Filed: Mar. 30, 2015

(86) PCT No.: PCT/EP2015/056859
§ 371 (c)(1),
(2) Date: Oct. 7, 2016

(87) PCT Pub. No.: WO2015/155044
PCT Pub. Date: Oct. 15, 2015

(65) Prior Publication Data
US 2017/0030870 A1 Feb. 2, 2017

(30) Foreign Application Priority Data

Apr. 9, 2014 (EP) .................................. 14001295

(51) Int. Cl.
*G01N 11/16* (2006.01)
*G01N 29/28* (2006.01)
(Continued)

(52) U.S. Cl.
CPC .............. *G01N 29/28* (2013.01); *G01N 9/34* (2013.01); *G01N 11/16* (2013.01); *G01N 29/04* (2013.01); *G01N 2009/006* (2013.01)

(58) Field of Classification Search
CPC .... G01N 29/28; G01N 2291/101; G01N 9/32; G01N 9/34; G01N 9/36; G01N 11/16;
(Continued)

(56) References Cited

U.S. PATENT DOCUMENTS 4,920,787 A  5/1990 Dual et al.
5,831,178 A  11/1998 Yoshimura et al.
(Continued)

FOREIGN PATENT DOCUMENTS

DE  102 35 322 A1  2/2004
DE  196 34 663 B4  11/2005
(Continued)

OTHER PUBLICATIONS

Communication dated Feb. 15, 2017, from European Patent Office (Third Party Observation) in counterpart application No. EP20150712650.
(Continued)

*Primary Examiner* — Lisa M Caputo
*Assistant Examiner* — Suman K Nath
(74) *Attorney, Agent, or Firm* — Sughrue Mion, PLLC

(57) ABSTRACT

A method to measure the vibrational characteristics of an oscillating system (1) uses a control system (6, 7a, 7b, 7c). The oscillating system comprises a resonator, at least one vibration exciter and at least one sensor. The resonator is excited by the vibration exciter, and the motion of the resonator is measured by the sensor. The control system uses the sensor to control the motion of the resonator by the vibration exciter. The motion of the resonator is a superposition of at least two harmonic motions, and the control system comprises at least two subcontrollers (7a, 7b, 7c). Each harmonic motion is controlled independently by one of
(Continued)

the subcontrollers. The harmonic motions are controlled by the subcontrollers simultaneously. A corresponding device is also disclosed.

24 Claims, 6 Drawing Sheets

(51) Int. Cl.
  *G01N 9/34* (2006.01)
  *G01N 29/04* (2006.01)
  *G01N 9/00* (2006.01)

(58) Field of Classification Search
  CPC ............ G01N 29/04; G01N 2009/006; G01N 2009/004
  USPC ........... 73/579, 662, 587, 602, 24.01, 24.05, 73/54.41, 64.53, 61.79, 61.49, 53.01, 73/23.28
  See application file for complete search history.

(56) References Cited

U.S. PATENT DOCUMENTS

| | | | |
|---|---|---|---|
| 5,837,885 | A | 11/1998 | Goodbread et al. |
| 5,885,496 | A | 3/1999 | Beane et al. |
| 7,716,995 | B2 | 5/2010 | Patten |
| 2003/0233868 | A1 | 12/2003 | Rieder et al. |
| 2003/0233878 | A1 | 12/2003 | Drahm et al. |

FOREIGN PATENT DOCUMENTS

| | | |
|---|---|---|
| EP | 1 058 820 B2 | 8/2016 |
| WO | 99/44018 A1 | 9/1999 |
| WO | 03/095950 A1 | 11/2003 |

OTHER PUBLICATIONS

Communication dated Dec. 11, 2017, from European Patent Office (Third Party Observation) in counterpart application No. EP20150712650.
R.M. Langdon, "Resonator sensors—a review", Journal of Physics E: Scientific Instruments, 1985, vol. 18, pp. 103-115.
C. Kharrat, E. Colinet, and A. Voda, "H∞ loop shaping control for pll-based mechanical resonance tracking in nems resonant mass sensors", IEEE Sensors Conference, 2008, pp. 1135-1138.
P. Rust, D. Cereghetti, and J. Dual, "A viscometric chip for DNA analysis", Procedia Engineering, vol. 47, pp. 136-139, 2012, 26th European Conference on Solid-State Transducers, Eurosensor 2012.
J. Dual and O. O'Reilly, "Resonant torsional vibrations: an application to dynamic viscometry", Archive of Applied Mechanics, vol. 63, No. 7, pp. 437-451, 1993.
T. M. Stokich, D. R. Radtke, C. C. White, and J. L. Schrag, "An instrument for precise measurement of viscoelastic properties of low viscosity dilute macromolecular solutions at frequencies from 20 to 500 kHz", Journal of Rheology, vol. 38, No. 4, pp. 1195-1210, 1994.
C. Blom and J. Mellema, "Torsion pendula with electromagnetic drive and detection system for measuring the complex shear modulus of liquids in the frequency range 80/2500 Hz", Rheologica Acta, vol. 23, pp. 98-105, 1984.
J. R. Vig, "Temperature-insensitive dual-mode resonant sensors—a review", Sensors Journal, IEEE, vol. 1, No. 1, pp. 62-68, 2001.
J. Sell, A. Niedermayer, and B. Jakoby, "A digital PLL circuit for resonator sensors," Sensors and Actuators A: Physical, vol. 172, No. 1, pp. 69-74, 2011.
Arnau, J. Garcia, Y. Jimenez, V. Ferrari, and M. Ferrari, "Improved electronic interfaces for AT-cut quartz crystal microbalance sensors under variable damping and parallel capacitance conditions", Review of Scientific Instruments, vol. 79, No. 7, pp. 075110-1 to 075110-12, 2008.
H. Tjahyadi, F. He, and K. Sammut, "Multi-mode vibration control of a flexible cantilever beam using adaptive resonant control," Smart Materials and Structures, vol. 15, No. 2, p. 270-278, 2006.
J. Kutin, A. Smrecnik, and I. Bajsic, "Phase-locking control of the coriolis meter's resonance frequency based on virtual instrumentation", Sensors and Actuators A: Physical, vol. 104, No. 1, pp. 86-93, 2003.
Gokcek, "Tracking the resonance frequency of a series RLC circuit using a phase locked loop", in Proceedings of 2003 IEEE Conference on Control Applications, 2003, pp. 609-613.
Kern, T. Brack, and W. Seemann, "Resonance tracking of continua using self-sensing actuators", Journal of Dynamic Systems, Measurement, and Control, vol. 134, No. 5, pp. 051004-1 to 051004-9, 2012.
S. Park, C.-W. Tan, H. Kim, and S. K. Hong, "Oscillation control algorithms for resonant sensors with applications to vibratory gyroscopes," Sensors, vol. 9, No. 8, pp. 5952-5967, 2009.
J. Gaspar, S. F. Chen, A. Gordillo, M. Hepp, P. Ferreyra, and C. Marqus, "Digital lock in amplifier: study, design and development with a digital signal processor", Microprocessors and Microsystems, vol. 28, No. 4, pp. 157-162, 2004.
Sell et al., "Digital phase-locked loop circuit for driving resonant sensors", Procedia Engineering 5 (2010) 204-207.
Krasser et al., "Simultaneous Measurements at U-tube Density Sensors in Fundamental and Harmonic Oscillation", EUROCON 2007 the International Conference on "Computer as a Tool", pp. 551-555.
International Search Report dated May 6, 2015, issued by the International Searching Authority in corresponding application No. PCT/EP2015/056859.
Wattinger, T.: Modeling and experimental study of a flexural vibration sensor for density measurements. Diss. ETH No. 21938 Zurich, 2014, pp. 69 to 70.
Brack T., Dual J.: Multimodal torsional vibrations for the characterization of complex fluids. Fluid Structure Interaction VII, Wit Transactions on the Built Environment, pp. 191 to 200.

(a) Simulation (b) Experiment

METHOD AND DEVICE FOR MULTIPLE-FREQUENCY TRACKING OF OSCILLATING SYSTEMS

TECHNICAL FIELD

The present invention relates to a method to measure the vibrational characteristics of an oscillating system using a control system, and to a corresponding device.

PRIOR ART

Reference is made to the following prior-art documents:

[1] R. M. Langdon, "Resonator sensors—a review," in *Journal of Physics E: Scientific Instruments* 18, vol. 18, no. 103, 1985.

[2] C. Kharrat, E. Colinet, and A. Voda, "H∞ loop shaping control for pll-based mechanical resonance tracking in nems resonant mass sensors," in *IEEE Sensors Conference*, 2008, pp. 1135-1138

[3] P. Rüst, D. Cereghetti, and J. Dual, "A viscometric chip for DNA analysis," *Procedia Engineering*, vol. 47, pp. 136-139, 2012, 26th European Conference on Solid-State Transducers, Eurosensor 2012.

[4] J. Dual and O. O'Reilly, "Resonant torsional vibrations: an application to dynamic viscometry," *Archive of Applied Mechanics*, vol. 63, no. 7, pp. 437-451, 1993.

[5] U.S. Pat. No. 4,920,787 to J. Dual, M. Sayir, and J. Goodbread.

[6] T. M. Stokich, D. R. Radtke, C. C. White, and J. L. Schrag, "An instrument for precise measurement of viscoelastic properties of low viscosity dilute macromolecular solutions at frequencies from 20 to 500 kHz," *Journal of Rheology*, vol. 38, no. 4, pp. 1195-1210, 1994.

[7] C. Blom and J. Mellema, "Torsion pendula with electromagnetic drive and detection system for measuring the complex shear modulus of liquids in the frequency range 80-2500 Hz," *Rheologica Acta*, vol. 23, pp. 98-105, 1984.

[8] J. R. Vig, "Temperature-insensitive dual-mode resonant sensors—a review," *Sensors Journal, IEEE*, vol. 1, no. 1, pp. 62-68, 2001.

[9] J. Sell, A. Niedermayer, and B. Jakoby, "A digital pll circuit for resonator sensors," *Sensors and Actuators A: Physical*, vol. 172, no. 1, pp. 69-74, 2011.

[10] A. Arnau, J. Garcia, Y. Jimenez, V. Ferrari, and M. Ferrari, "Improved electronic interfaces for at-cut quartz crystal microbalance sensors under variable damping and parallel capacitance conditions," *Review of Scientific Instruments*, vol. 79, no. 7, pp. 075110-075110-12, 2008.

[11] H. Tjahyadi, F. He, and K. Sammut, "Multi-mode vibration control of a flexible cantilever beam using adaptive resonant control," *Smart Materials and Structures*, vol. 15, no. 2, p. 270, 2006.

[12] J. Kutin, A. Smrečnik, and I. Bajsić, "Phase-locking control of the coriolis meters resonance frequency based on virtual instrumentation," *Sensors and Actuators A. Physical*, vol. 104, no. 1, pp. 86-93, 2003.

[13] C. Gökcek, "Tracking the resonance frequency of a series RLC circuit using a phase locked loop," in *Proceedings of 2003 IEEE Conference on Control Applications*, 2003, pp. 609-613.

[14] D. Kern, T. Brack, and W. Seemann, "Resonance tracking of continua using self-sensing actuators," *Journal of Dynamic Systems, Measurement, and Control*, vol. 134, no. 5, p. 051004, 2012.

[15] S. Park, C.-W. Tan, H. Kim, and S. K. Hong, "Oscillation control algorithms for resonant sensors with applications to vibratory gyroscopes," *Sensors*, vol. 9, no. 8, pp. 5952-5967, 2009.

[16] U.S. Pat. No. 5,837,885 to J. Dual, J. Goodbread, K. Häusler and M. Sayir.

[17] J. Gaspar, S. F. Chen, A. Gordillo, M. Hepp, P. Ferreyra, and C. Marqus, "Digital lock in amplifier: study, design and development with a digital signal processor," *Microprocessors and Microsystems*, vol. 28, no. 4, pp. 157-162, 2004

Since the eigenfrequencies and damping parameters of an oscillating system are characteristic values which are dependent both on the system properties as well as on external influences, measuring these frequencies has led to the widespread principle of resonant sensors [1]. It has become a common technique in research as well as in industry to permanently track one resonance frequency using appropriate control structures. This allows to generate an output (i.e. the frequency or frequency change) which can be related to the desired physical quantity. Such applications can be found in quartz crystal microbalances or in micro electro mechanical systems (MEMS), for example as mass sensors [2] or as biosensors [3]. In the field of fluid characterization, the frequency tracking provides an efficient approach for the development of an on-line viscometer. This has been successfully realized by measuring the damping of a vibrating structure which is in contact with a fluid [4, 5]. All these applications can only track one single frequency. However, in many applications the investigation of more values is required, whether as investigation of frequency dependent behavior, as redundancy values to improve the measurement accuracy or as basis for compensation of errors. This can be achieved by consecutively tracking particular resonance frequencies of a continuous oscillator [6] or by simply using several oscillators [7]. Both methods, though, show several disadvantages. The former case limits the application to the detection of slowly changing processes, since the consecutive tracking is time consuming. On the other hand, the latter case does not ensure measuring the exact same condition (e.g. temperature), since the sensors are spatially separated and may have different properties.

SUMMARY OF THE INVENTION

It is an object of the present invention to overcome these shortcomings of the prior art.

In a first aspect, the present invention provides a method to measure the vibrational characteristics of an oscillating system using a control system, said oscillating system comprising a resonator, at least one vibration exciter and at least one sensor, said resonator being excited by said vibration exciter, the motion of said resonator being measured by said sensor, said control system using said sensor to control said motion of said resonator by said vibration exciter, said motion of said resonator being a superposition of at least two harmonic motions, said control system comprising at least two subcontrollers, said at least two harmonic motions being controlled independently by said at least two subcontrollers, respectively, and said harmonic motions being controlled by said subcontrollers simultaneously.

The harmonic motions will in general have different frequencies. In other words, the invention proposes to track multiple frequencies of one single oscillator simultaneously with the aid of multiple separate subcontrollers.

The method of the present invention can also be expressed as follows: A method to measure the vibrational characteristics of an oscillating system using a control system, said oscillating system comprising a resonator, at least one vibration exciter and at least one sensor, the method comprising:

exciting the resonator by said at least one vibration exciter;

measuring the motion of said resonator by said at least one sensor; and operating said control system to control said motion of said resonator by said at least one vibration exciter, using said at least one sensor, wherein said motion of said resonator is a superposition of at least two harmonic motions, in particular, harmonic motions having different frequencies, wherein said control system comprises at least two subcontrollers, and wherein said at least two harmonic motions are controlled independently by said at least two subcontrollers, said harmonic motions being controlled by said subcontrollers simultaneously.

The subcontrollers are advantageously implemented as phase-locked loops. In other words, the subcontrollers are configured to keep a predetermined phase relationship between the harmonic excitation and the harmonic motion of the resonator in response to the harmonic excitation.

Each of said harmonic motions preferably has a frequency close to (i.e., at or near) a resonance frequency of the resonator. Here, "close to a resonance frequency" is to be interpreted as being sufficiently close to a resonance frequency such that the slope of the phase response is sufficiently high and the amplitude of said harmonic motion is sufficiently high to be processed by said subcontroller. This can be formulated, e.g., as the frequency being in the range of $\omega \in [\omega_{res} \pm 3\Delta\omega]$ where $\Delta\omega$ is the bandwidth of the resonance, cf. FIG. 1. Advantageously, the resonance frequencies of the resonator are sensitive to properties of a fluid, being in contact with said resonator. In this manner, the method of the present invention can be employed to determine at least one property of a fluid that is in contact with the resonator.

In exemplary embodiments, these properties may include the density and/or the viscosity and/or viscoelastic properties of the fluid.

In particular, both density and viscosity of a fluid may be determined if at least one harmonic motion is a bending vibration of a resonator that is in contact with the fluid, and at least one other harmonic motion is a torsional oscillation of the same resonator. In [Wattinger, T. Modeling and experimental study of a flexural vibration sensor for density measurements. Diss. ETH No. 21938 Zurich, 2014, pages 69 to 70] the influence of Newtonian fluids on bending vibrations of a cylindrical structure was investigated. It was found that this influence of the fluid depends, in a first approximation, only on the density of the fluid, whereas the viscosity plays only a minor role (see Eq. 4.17 of the reference on pages 69-70). Therefore the simultaneous control of a bending vibration and of a torsional oscillation is an interesting concept for determining both the density and the viscosity of a fluid. By measuring the resonance frequency of the bending vibration, the density can be determined. The resonance frequency of the torsional oscillation depends on both density and viscosity; when density is known, viscosity can be determined. Separate transducers (vibration exciters) are advantageously employed to excite bending vibrations and torsional oscillations, respectively. However, many known sensors are sensitive to both bending vibrations and torsional oscillations, and it is advantageous to use a common sensor for measuring these two types of oscillations.

Viscoelastic properties of a fluid may be determined by measuring a resonance frequency shift of at least one mode of the resonator due to the presence of the fluid, and by measuring a change of the damping of at least one mode of the resonator due to the presence of the fluid. A method for measuring the damping of a mode of the resonator is explained in more detail below. In the conference paper [Brack T., Dual J.: Multimodal torsional vibrations for the characterization of complex fluids. *Fluid Structure Interaction VII*, Wit Transactions on the Built Environment, pp. 191-200, 2013], the relationship between resonance frequency $\omega$ and damping $\delta$ of a linear oscillator in contact with a linear viscoelastic fluid is described. In that paper, the following approximate relationships are presented:

$$\Delta\omega_n^2 = a_n \cdot \rho f \omega_{res,n,0} \cdot (\eta' - \eta'')$$

$$\Delta\delta_n^2 = a_n \cdot \rho f \omega_{res,n,0} \cdot (\eta' + \eta'') \quad (1)$$

Here, $\Delta\omega_n$ is the shift of the resonance frequency $\omega_{res,n,0}$ of mode n due to the presence of the fluid, and $\Delta\delta_n$ is the change of the damping of mode n due to the presence of the fluid. The factor $a_n$ is a mode-dependent sensor constant. The parameters $\eta'$ and $\eta''$ are the two components of the complex viscosity; they describe viscosity and elasticity of the fluid. These two quantities are frequency-dependent material properties. Assuming that the density $\rho_f$ of the fluid is known, the two parameters $\eta'$ and $\eta''$ can be determined by measuring the two parameters $\Delta\omega_n^2$ and $\Delta\delta_n^2$.

Since $\eta'$ and $\eta''$ are frequency-dependent quantities, prior-art resonance sensors are only of limited use for characterizing viscoelastic fluids, as usually only a single frequency can be observed. By observing several frequencies simultaneously, the utility of resonance sensors for determining viscoelastic properties of fluids can be much increased. Because measurements can be performed very quickly, even dynamic changes of the viscoelastic properties can be determined at multiple frequencies. This has hitherto not been possible, neither with classical rheometers nor with resonance sensors.

In other exemplary embodiments, the method of the present invention can be employed to determine the mass flow of a fluid through a resonator having a tube-like structure, as in a Coriolis mass flow meter. Coriolis mass flow meters are known per se. In a Coriolis mass flow meter, a fluid is passed through a flow tube, and a bending vibration of the flow tube is observed. The Coriolis forces on the fluid cause a position-dependent phase shift of the bending vibration. This phase shift is measured, and the mass flow can be derived from the phase shift. Furthermore, the density of the fluid can be determined by measuring the resonance frequency of the bending vibration, since the resonance frequency depends on the combined mass of the tube and the fluid contained in it. In summary, the vibration behavior of the resonator (including its resonance frequencies) is sensitive to the mass flow. By measuring several bending modes simultaneously, the precision of such mass flow and/or density measurements can be improved. By additionally exciting torsional oscillations, the viscosity of the fluid can additionally be determined. The bending modes and/or torsional oscillations are advantageously simultaneously controlled by the presently proposed method.

In some embodiments, the vibration exciter(s) and the sensor(s) can be separate units. In other embodiments, a single transducer can act as both a vibration exciter and a sensor. For instance, an electromagnetic transducer can act both as an actuator for exciting vibrations and as a sensor for measuring the thus-excited vibrations. In such cases, it is advantageous if at least one of the phase-locked loops is implemented as a gated phase-locked loop containing at least one switch, in particular, as in patent U.S. Pat. No. 5,837,885, so as to enable a timewise separation of excitation and detection. In the alternative, some or all of the subcontrollers can have individual inputs connected to form a common input and have individual outputs, the individual outputs being connected to an adder having a common output, and the common input and/or the common output can be gated by switches. A gated implementation is particularly advantageous if a single transducer acts both as a vibration exciter and a sensor, but may be advantageous also in other contexts.

In some embodiments, the subcontrollers are used with two different reference phase settings to measure the damping of the resonator in the vicinity of one resonance frequency.

The subcontrollers may be used to measure the amplitudes of said harmonic motions. This is particularly useful in applications where the response of the resonator is nonlinear.

In a second aspect, the present invention provides a device for measuring the vibrational characteristics of an oscillating system, the device comprising said oscillating system and a control system, said oscillating system comprising a resonator, at least one vibration exciter and at least one sensor, the resonator being coupled to the vibration exciter for exciting a motion of the resonator, the sensor being configured to measure said motion of the resonator, the control system being configured to control the motion of the resonator via the vibration exciter using the sensor, wherein the motion of the resonator is a superposition of at least two harmonic motions, the control system comprising at least two subcontrollers, each of said subcontrollers being configured to independently control one of said harmonic motions, the subcontrollers being configured to control said harmonic motions simultaneously.

As mentioned above, each of said subcontrollers can comprise a phase-locked loop. Each of said subcontrollers can be configured to control a harmonic motion that has a frequency close to (i.e., at or near) a resonance frequency of said resonator. Said resonator can have a plurality of resonance frequencies, said resonance frequencies being sensitive to properties of a fluid that is in contact with said resonator. Said fluid properties can include density and/or viscosity and/or viscoelastic properties of said fluid. In some embodiments, the resonator can be a tube-like structure, and its vibration behavior (including its resonance frequencies) can be sensitive to a mass flow of a fluid through said tube-like structure. At least one of the phase-locked loops can be a gated phase-locked loop containing at least one switch. In the alternative, some or all of the subcontrollers can have individual inputs connected to form a common input and can have individual outputs, the device can comprise an adder having inputs that are connected to the individual outputs of said subcontrollers and having a common output, and the device can comprise one or more switches for gating the common input and/or the common output. In some embodiments, said subcontrollers can be configured to operate with two different reference phase settings to measure the damping of the resonator. The subcontrollers can be configured to measure the amplitudes of said harmonic motions.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

It is beneficial to track multiple frequencies of one single oscillator simultaneously. The multi-mode control has become an object of research in the field of crystal oscillators to overcome accuracy problems [8] or as compensation of the parasitic capacitance of piezoelectric crystals [9,10]. Multi-mode techniques are also used to actively damp several vibration modes of a structure [11].

Based on the integration of an oscillator in a phase-locked loop (PLL), which has been successfully investigated by numerous research groups [2,12-15], the present invention claims a novel control concept that allows the simultaneous tracking of multiple frequencies of an oscillating system. These frequencies could be the resonance frequencies or any other frequencies that lie near the resonance value. The PLL could also be used in a gated fashion as described in patent U.S. Pat. No. 5,837,885.

Figure 1:
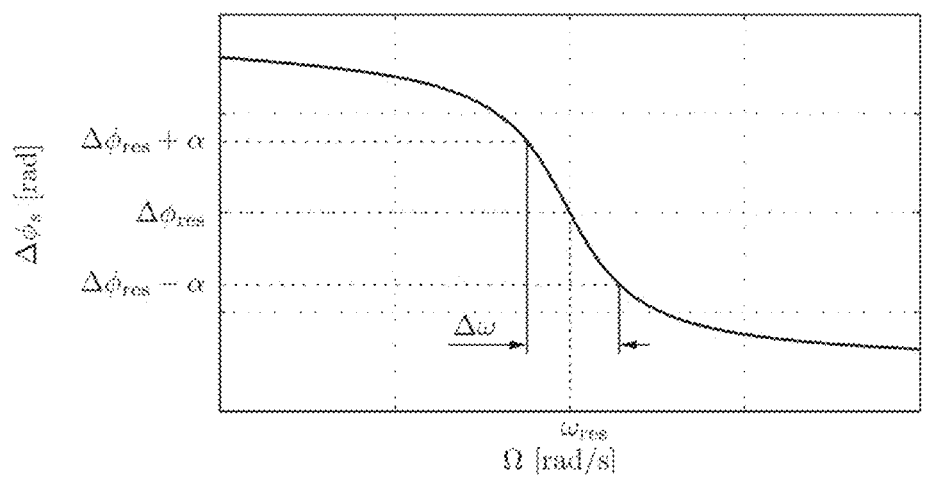
FIG. 1 shows steady state phase shift $\Delta\phi_s$ of a single degree of freedom oscillator around the resonance frequency $\omega_{res}$.

In every linear oscillating system, the stationary phase shift between a harmonic excitation and the response signal is an amplitude independent and unique function around the resonance frequency, as it is shown in FIG. 1. It is therefore beneficial to use the phase shift to control the exciting frequency to maintain the system at resonance or at any other state that is related to a specific phase shift value. This can be achieved by the integration of the oscillating system with a phase-locked loop (PLL).

Figure 2:
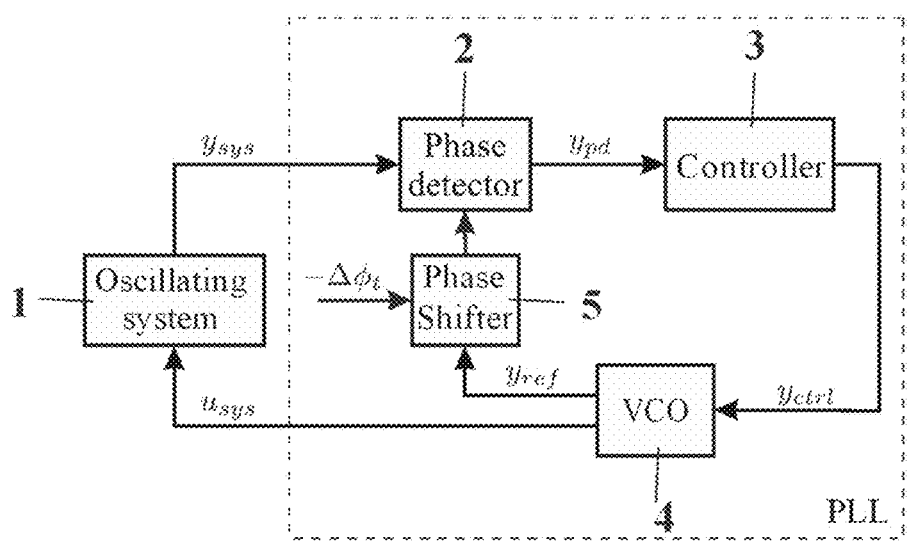
FIG. 2 shows the setup of a phase-locked loop in combination with an oscillating system. The elements of the PLL are framed by the dashed line.

A conventional PLL is shown in the dashed box of FIG. 2. It consists of a phase detector 2, a controller 3 (often denoted as filter) and a voltage controlled oscillator (VCO) 4. The VCO generates a periodic signal (e.g. square, triangle or harmonic wave) whose frequency follows the frequency of the incoming signal of the PLL, leaving a certain phase difference as controller offset. Hence the conventional PLL takes a frequency modulated signal as input and returns the modulation signal as output. There is no oscillating system within the feedback. But since the functionality of the PLL bases upon the phase detection between two harmonic signals, it can be used in conjunction with an oscillating system 1 as shown in the block diagram in FIG. 2. The periodic VCO output is led to the oscillating system as excitation $u_{sys}$. The phase detector measures the phase shift $y_{pd}$ between the output of the oscillating system $y_{sys}$ and a possibly phase shifted reference signal $y_{ref}$ of same frequency. A phase shifter 5 shifts the phase of the reference signal by $-\Delta\phi_t$. By tuning the frequency of the VCO using the controller output $y_{ctrl}$, the excitation frequency is varied until the controller input is zero, which is related to the phase shift of the oscillating system (i.e. phase shift between $u_{sys}$ and $y_{sys}$) being equal to the predefined phase shift value $-\Delta\phi_t$. This system can be used to actively track the resonance frequency or any other frequency that is related to a unique phase shift value. The damping can be measured by extracting the frequencies that are related to the phase shift values of $\Delta\phi_{res} \pm \alpha$. This concept has been used in Patent U.S. Pat. No. 5,492,0787 and 5,837,885.

Oscillating systems might exhibit multiple vibration modes, each with a specific resonance frequency. If the resonance frequencies are clearly separated, the modes have almost no interaction. Hence every single mode can be regarded as an independent one degree of freedom system. Therefore multiple frequency bands exist where the phase shift shows the behavior described in FIG. 1.

The present invention describes a method that enables the simultaneous control of multiple frequencies by means of the described phase-locked loop method. Independent of the number of controlled frequencies, only two transducers are necessary, one to generate the excitation $u_{sys}$ and one to detect the output $y_{sys}$. If the system is used in a gated fashion as in U.S. Pat. No. 5,837,885, only one transducer can be used alternately as sensor or actuator.

This enables a variety of novel possibilities in measurement instrumentation, especially in the field of fluid characterization. For example:

Viscometry. The tracking of one frequency is a common method in industrial viscometry applications. The tracking of multiple frequencies increases the accuracy of such devices.

Rheology. In this field a lot of instruments have been investigated that aim to characterize a fluid at several frequencies. The necessary data is up to now only consecutively accessible. The presented invention enables to gather all information simultaneously.

General resonance sensor methods. The use of multiple frequencies can also be used to compensate for unwanted influences, for example due to temperature effects.

Simultaneous measurements of several different fluid properties, each of which might influence the different modes to various degrees. A rod can be used in a bending mode and a torsional mode in a fluid, where density and viscosity are influencing the resonance frequency and damping in different ways.

Figure 3:
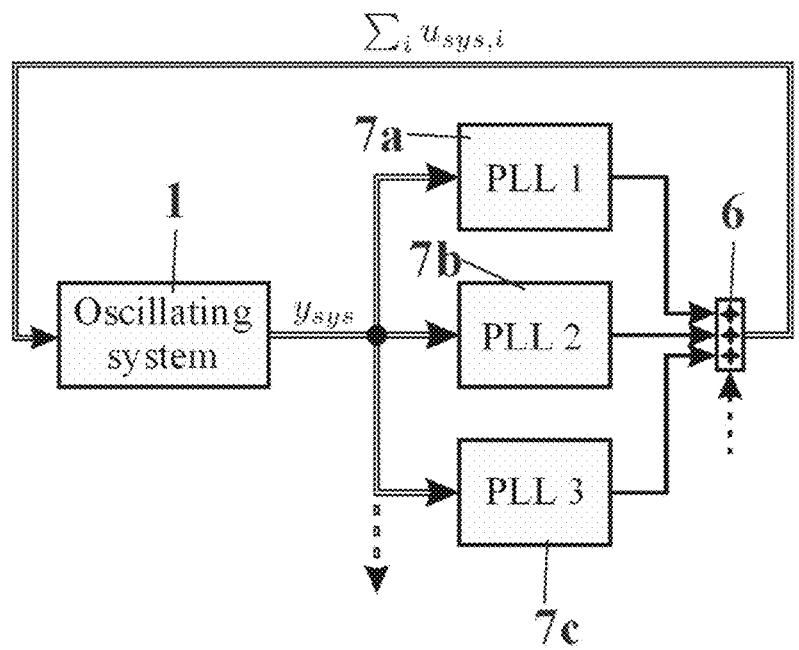
FIG. 3 shows a control concept of the simultaneous excitation and control of multiple frequencies of an oscillating system.

For the simultaneous tracking of multiple frequencies a parallel arrangement of multiple PLLs 7 can be used, each generating a periodic single-frequency signal as illustrated in FIG. 3. The output signals of the particular PLLs are added together in an adder 6 and form the multi-frequency excitation signal $\Sigma_i u_{sys,i}$. Consequently, the output of the oscillating system $y_{sys}$ is a signal composed of the particular frequencies. Hence an effective frequency separation in each PLL is of utmost importance.

Figure 5:
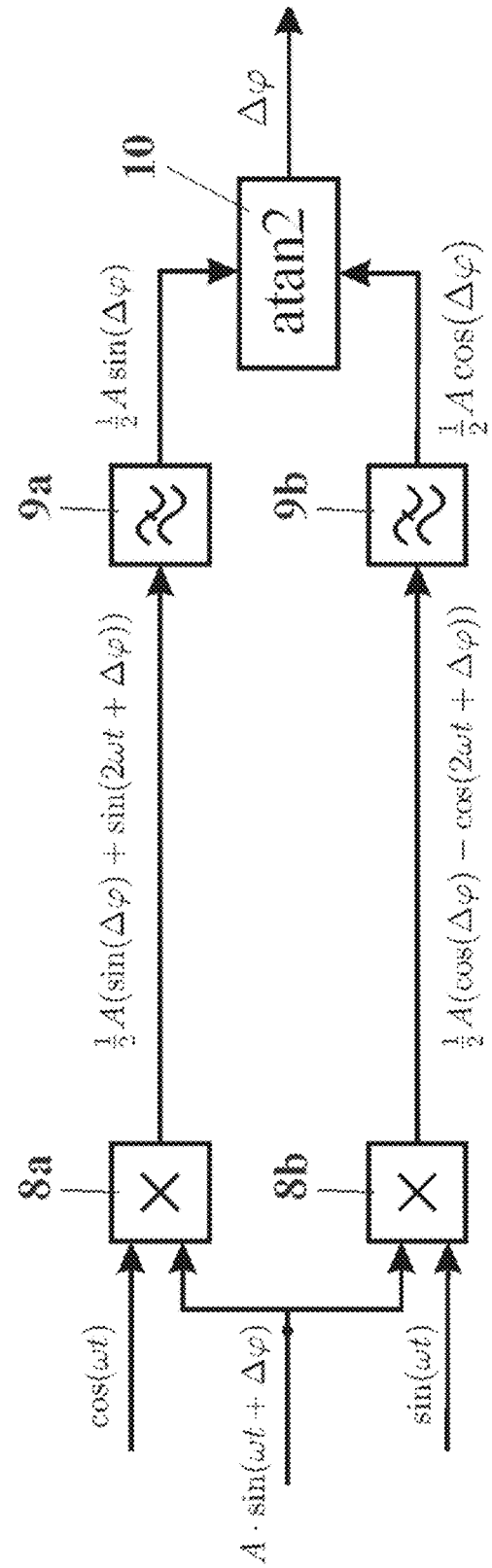
FIG. 5 shows a block diagram of an averaging phase detector, consisting of two multiplications 8, two low-pass filters 9 and an atan2 function block 10.

Using a special kind of phase detector, namely a digital averaging phase detector (APD) in each PLL, one can combine this task and the phase detection. The APD is used in various applications e.g. in digital lock-in amplifiers [17]. The working principle is shown in FIG. 5. The APD multiplies its input signal, which can be described by $A \sin(\omega t + \Delta\phi)$ in steady state, both with a sine and cosine signal of the same frequency. Hence two reference signals $\cos(\omega t)$ and $\sin(\omega t)$ are necessary. After the multiplications 8 a low-pass filter 9 follows, whose cutoff frequency is much smaller than the exciting frequency. Performing the atan2 function 10 using the output signals of the low-pass filters, the phase difference $\Delta\phi$ is computed. The atan2 function is defined through $$\mathrm{atan2}(y, x) = \begin{cases} \arctan\left(\frac{y}{x}\right), & x > 0 \\ \arctan\left(\frac{y}{x}\right) + \pi, & y \geq 0, x < 0 \\ \arctan\left(\frac{y}{x}\right) - \pi, & y < 0, x < 0 \\ +\frac{\pi}{2}, & y > 0, x = 0 \\ -\frac{\pi}{2}, & y < 0, x = 0 \\ \text{undefined}, & y = 0, x = 0 \end{cases}$$

The APD acts as a very effective band-pass filter which enables the effective frequency separation.

While the use of an APD for frequency separation and phase detection is advantageous, it is not the only possibility. For instance, instead of an APD, any of the following may be used: (a) A conventional band pass filter followed by any kind of conventional phase detector (computationally expensive and well-suited only if frequencies are sufficiently well separated); or (b) a so-called single-point discrete Fourier transform (DFT), i.e., a variant of a DFT that computes only a single spectral component, the most important single-point DFT algorithm being the Goertzel Algorithm.

Figure 6:
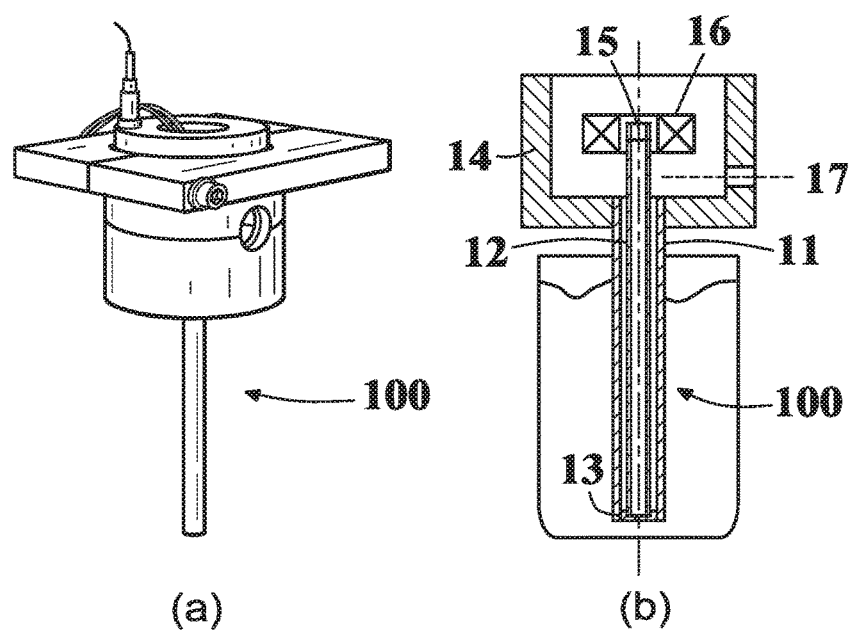
FIG. 6 illustrates an oscillating system comprising a torsional resonator, electromagnetic excitation and optical readout.—a) Photo of the setup; b) Section view.
Figure 7:
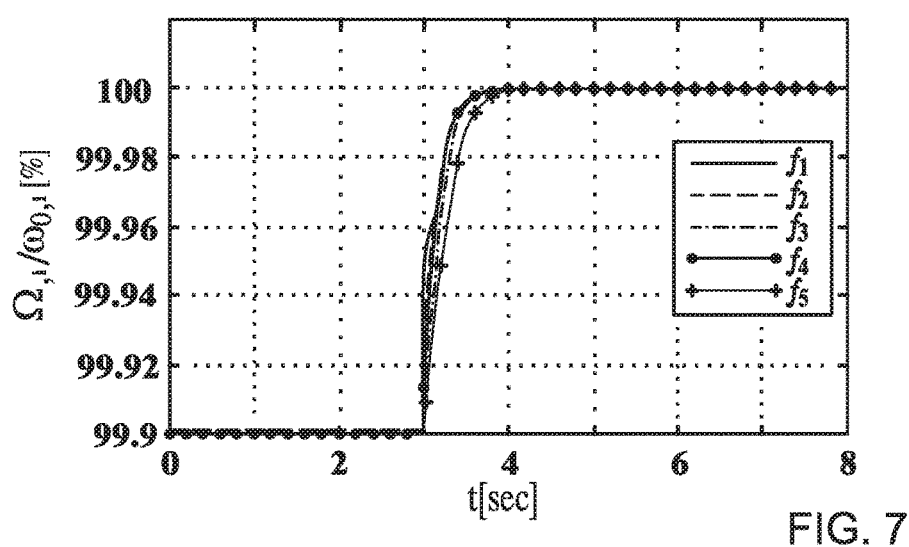
FIG. 7 is a diagram showing an experimental result of the simultaneous tracking of five resonance frequencies of the oscillating system depicted in FIG. 6.

The mechanical resonator which is used as oscillating system can be a torsional resonator originally used for viscosity measurements. FIG. 6 shows a torsional resonator 100 that is composed of two hollow cylinders. The outer cylinder 11 is fixed at one end to the body 14 and represents the part that is in contact with a fluid. It is closed at the end with an end piece 13, to which a second tube 12 is fixed. The second tube 12 leads inside the outer tube 11 back into the body 14. On top of tube 12 a permanent magnet 15 is mounted. Using a coil system 16 that is arranged around the magnet position, the excitation moment is applied electromagnetically. The movement is detected optically using a single-point laser vibrometer 17. Alternatively the same transducer can be used for the detection using a gated PLL as disclosed in U.S. Pat. No. 5,837,885. The laser beam points on the inner cylinder 12, whereas the position is selected to be as near as possible to the excitation. The outer tube 11 has a length of $l_o$=100 mm, an outer diameter of $d_o$=9.5 mm and a wall thickness of $t_o$=0.335 mm. The inner tube 12 measures length $l_i$=135 mm, outer diameter $d_i$=7 mm and wall thickness $t_i$=0.45 mm. Experimental results, depicted in FIG. 7, show the effective simultaneous control of the first five resonance frequencies of the system. The control loop is implemented on a TMS320C6747 floating point digital signal processor (DSP) from Texas Instrument which is integrated in the OMAP-L137 Evaluation Module from Spectrum Digital.

The operation of the invention is described in the following figures.

In FIG. 1, the steady state phase shift $\Delta\phi_s$ between a harmonic excitation signal of frequency $\Omega$ and the response of the oscillating system is shown exemplarily in the region of the resonance frequency $\omega_{res}$. The depicted situation represents a linear single degree of freedom oscillator and also continuous oscillating systems with many resonance frequencies, as long as these resonance frequencies are well separated. The slope of the curve is related to the damping of the system (i.e. of the particular vibration mode), characterized by the frequency difference $\Delta\omega$ corresponding to the phase shift values of $\Delta\phi_{res}\pm\alpha$.

FIG. 2 presents the phase-locked loop in conjunction with an oscillating system 1. Both the excitation signal $u_{sys}$ and the reference signals $y_{ref}$ are created by the VCO 4, whose frequency is varied by the output $y_{ctrl}$ of the controller 3. The phase detector 2 closes the loop by detecting the phase shift $y_{pd}$ of the system output and the phase shifted reference.

FIG. 3 presents the concept of the multimode control. The particular PLLs 7a, 7b, 7c etc. are of the same structure as the PLL in FIG. 2. The phase detectors are designed such that they extract the phase shift only at one particular frequency. These frequencies are the known excitation frequencies. A single line in the figure represents a harmonic signal containing a single frequency, a double line represents the signal, where multiple frequencies are superimposed.

Figure 4:
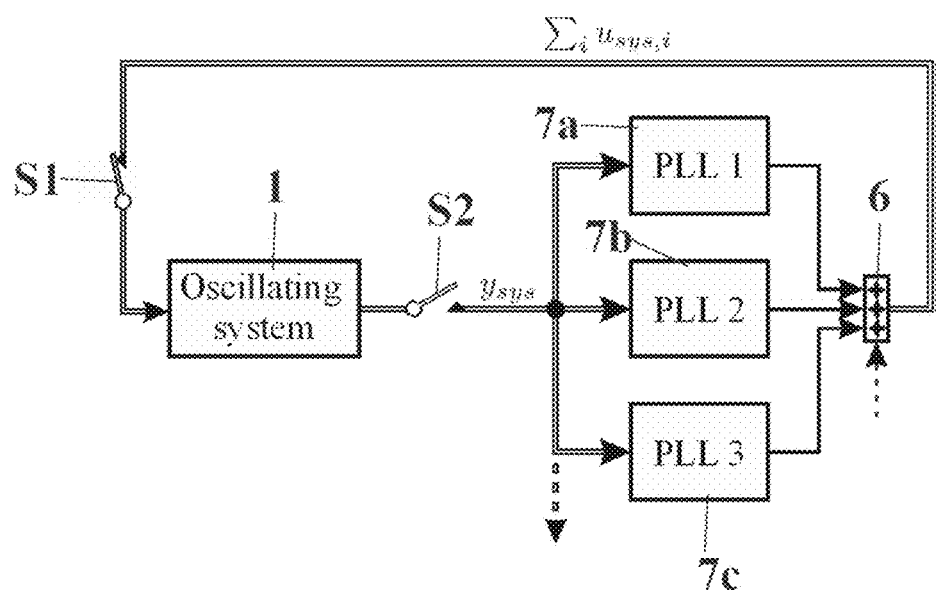
FIG. 4 shows a control concept of the simultaneous excitation and control of multiple frequencies of an oscillating system. By alternating between excitation and readout phase only one single transducer is necessary.

FIG. 4 presents the concept of the multimode control used in a gated fashion. The functionality remains the same, but the gated PLL uses the same transducer alternately for excitation or readout (see patent U.S. Pat. No. 5,837,885). By means of two switches S1 and S2 the process alternates continuously between excitation (S1 closed, S2 open) and readout phase (S1 open, S2 closed). The timing of the switches has to be adapted to the processed frequencies. Also a waiting time might be introduced between the excitation and readout phases.

FIG. 5 presents the working principle of the averaging phase detector. Due to the two multiplications 8a and 8b of the system output with a sine and cosine signal of the same frequency (which is known since it is the VCO frequency) it is possible to extract the phase shift at that particular frequency. The requirements on the low-pass filters 9 are low, since they only have to attenuate the component of double excitation frequency resulting from the multiplication.

FIG. 6 shows the oscillating system 1 comprising the resonator, electromagnetic excitation and optical readout. The sensor design is shown in FIG. 6a as a section view. The invention can be applied to every oscillating system that exhibits multiple vibration modes with separated resonance frequencies.

FIG. 7 depicts the experimental results. The graph shows the development of five frequencies of the torsional oscillator in air at 22° C. The frequencies, damping and resonance phase shift values of the torsional oscillator are given in Table I below. The frequencies start at 0.1% below the resonance value and develop simultaneously to the exact resonance values within 1 second. The resonance values have been measured before by means of traditional methods. The control process starts at t=3 sec, the frequency values are represented as relative values, with the particular resonance frequency as reference.

TABLE I

Resonance frequencies $\omega_0$ and damping ratio D of the torsional resonator in air at 22° C.

| Mode number | $\omega_0$ [Hz] | D [$10^{-5}$] |
| --- | --- | --- |
| 1 | 2588.95 | 5.33 |
| 2 | 5588.51 | 5.25 |
| 3 | 11190.01 | 10.08 |
| 4 | 13918.81 | 7.37 |
| 5 | 19269.07 | 5.48 |

Possible Measurement Concepts:

Concept 1: The simultaneous tracking of multiple resonance frequencies. This can be used in resonance sensors or to gain high efficiency in actuator applications.

Concept 2: Method for the fast and exact determination of the damping which uses the simultaneous control of the phase shift values of two different modes (denoted by the subscripts 1 and 2): $\Delta\phi_1=\Delta\phi_{res,1}-\alpha$ and $\Delta\phi_{res,2}+\alpha$. The achieved frequency difference $\Delta f_{large}=f(\Delta\phi_2)-f(\Delta\phi_1)$ is a measure for the damping. Alternatively, one particular mode can be driven at two different phase shift values.

Concept 3: When using a torsional oscillator that is clamped at one end and surrounded by a fluid, it can be shown that the fluid influence is very weak at $$\Delta\phi = \Delta\phi_{res} - \frac{\pi}{4}.$$

This fact enables to measure the properties of the oscillator itself even if a fluid is present, which could be used for temperature measurements. During multi-mode control this feature can be used as temperature reference.

Concept 4: The APD is also capable to extract the amplitude of the input signal by using the formulation $A=2\sqrt{X^2+Y^2}$, where X and Y are the output signals of the low-pass filters 9a and 9b, respectively. Therefore the presented invention enables also the simultaneous control of the vibration amplitudes of the oscillator which is very useful in the field of rheology (in rheology, the system response is generally non-linear and therefore depends on the excitation amplitude).

Additional Explanations Concerning Concept 2

The determination of damping is an important issue in many applications, especially in the field of viscometry. Two frequency values at known phase shifts $\pm\alpha$ around the resonance are needed to calculate the damping or, equivalently, the Q-factor of a specific mode. These two frequency values are usually evaluated one after another by consecutively changing the reference phase. Using the presently proposed method one can obtain the damping value directly by controlling the two required frequency values simultaneously. This is called direct damping measurement in what follows. In contrast to the simultaneous resonance tracking, the frequencies that have to be processed correspond in this case to the same vibration mode. Hence they will be very close together, depending on the resonance frequency and damping ratio of the investigated mode, which puts high demands on the APD.

Since the system is assumed to be linear, the superposition principle holds, and it is therefore possible to excite one mode with a two-frequency signal, of which the frequencies follow the phase shift target of $\Delta\phi_1=\Delta\phi_{res}-\alpha$ and $\Delta\phi_2=\Delta\phi_{res}+\alpha$, respectively.

In contrast to the simultaneous tracking of multiple resonances, in the present application the two frequencies are not well separated. It has therefore to be ensured that the frequency separation works properly nonetheless. This can be achieved by maximizing the frequency difference, hence $\alpha$ is advantageously set to 45°.

In an example, the damping was increased by immersing the sensor in a calibration oil of constant dynamic viscosity $\eta=8.18$ mPas at 22° C. The damping of the first mode was therefore increased by a factor of 10 ($Q_{fluid}=920$). However, the two frequencies were still very close-by, which required a relatively high-order filter. The filters were therefore implemented as 2nd order Butterworth low-pass filter with $\omega_{3\,dB}=2\pi0.1$ Hz. Obviously, the center frequencies $f_c$ of the filters should initially be set so that the two frequencies do not have the same value during the process. In the present example, the initial center frequencies were set to $f_c.f_i\pm10$ Hz. The controller parameters were adjusted as explained below, using a time constant of $T_c=2$ sec.

Figure 8:
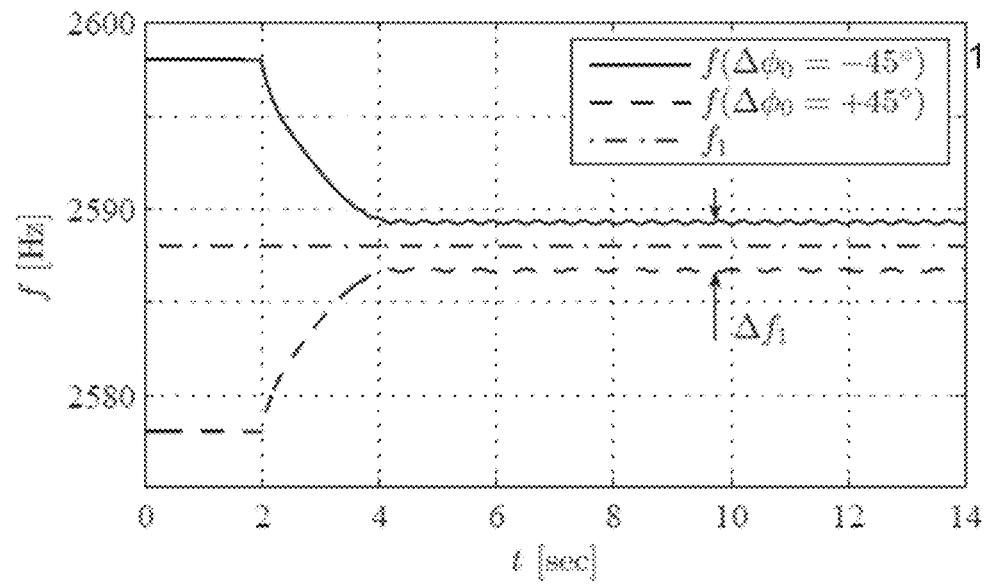
FIG. 8 is a diagram showing the time history of two frequencies starting at $f_1 \pm 10$ Hz and developing so that the final phase shift values equal $\Delta\phi_{1,2}=\Delta\phi_{res}\pm\alpha$. (a) Simulation result; (b) Experimental result.
Figure 8:
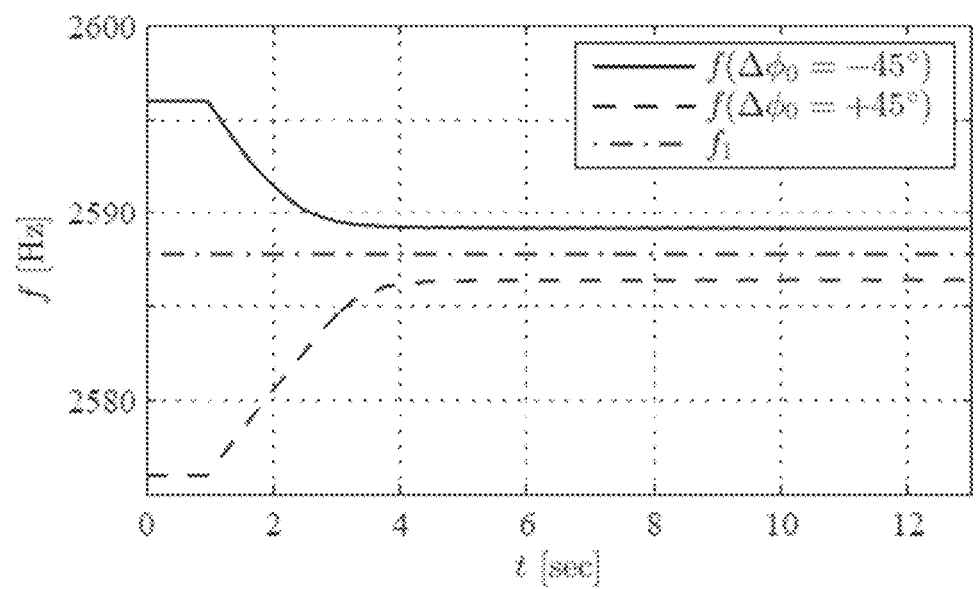

FIG. 8 shows simulation and experimental result of the frequency tracking for the direct damping measurement. The frequencies reached the final value after approximately four seconds and were stable with only small variations.

From the frequency difference $\Delta f_i$ the damping can directly be calculated using the following equation:

$$Q_i = \frac{\omega_{0,i}}{\Delta\omega_i}\tan\alpha$$

Here, $\Delta\omega_i=2\pi\Delta f_i$ is the angular frequency difference of mode i, and $\omega_{0,i}$ is the resonance frequency of mode i.

Averaging $\Delta f_1$ over the last two seconds yielded a Q-Factor of 920, in very close agreement with simulation results.

The result shows that the method is generally capable to separate frequencies even if they lie very close together, which can be used for the direct damping measurement. However, the closer the frequencies come together, whether due to low damping or a small $\alpha$, the more difficult the calculation of the Q-factor gets.

Additional Explanations Concerning Concept 3

The torsion angle $\Phi$ of a harmonically excited, linear torsional oscillator under the influence of a fluidic force $F_{fluid}$ can be described by the differential equation $$\ddot{\Phi}(t)+2\cdot\delta\cdot\dot{\Phi}(t)+\omega_0^2\cdot\Phi(t)=F_0\exp(i\Omega t)+F_{fluid},$$

wherein $\omega_0$ is the resonance frequency and $\delta$ the exponential decay rate of the oscillator without fluid. $\Omega$ is the excitation frequency. The influence of a Newtonian fluid on a circular cross section can approximately be described by the force $$F_{fluid}=-k(1+i)\dot{\Phi}(t),$$

where k is the fluid influence factor that depends both on the density and the viscosity of the fluid. Hence $F_{fluid}$ can be interpreted as an additional damping and mass. The steady-state phase shift between excitation force and coordinate $\Phi(t)$ is:

$$\Delta\phi = \operatorname{atan}\left(\frac{\Omega^2\cdot\Omega\cdot k-\omega_0^2}{\Omega(k+2\cdot\delta)}\right)$$

Solving the equation for $\Omega$ at $$\Delta\phi = -\frac{3}{4}\pi,$$

one obtains:

$$\Omega\left(\Delta\phi=-\frac{3}{4}\pi\right) = -\delta+\frac{1}{2}\sqrt{4\delta^2+4\omega_0^2}.$$

This expression is independent of the fluid influence factor k. Therefore the frequency that belongs to a phase shift of $$-\frac{3}{4}\pi$$

is independent of the properties of the fluid.

Figure 9:
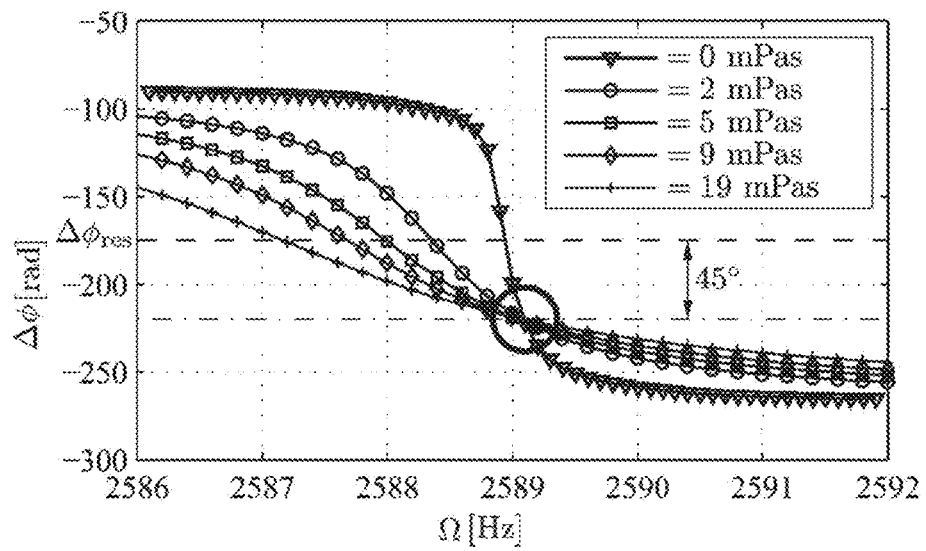
FIG. 9 is a diagram showing experimentally determined phase shift curves of a torsional oscillator under the influence of fluids with different viscosities.

This is illustrated in FIG. 9, which shows experimentally determined phase shift curves of a torsional oscillator under the influence of fluids with different viscosities. Due to parasitic phase shifts, the resonance is at a phase shift of approximately −175° (dashed line). Relative to the phase shift at resonance, the phase shift independent of k is at $$\Delta\phi = \Delta\phi_{res}-\frac{\pi}{4}\text{(dash-dotted line)}.$$

The frequency at which this phase shift occurs can be used to determine influences on the sensor that are not caused by the fluid, even when the sensor is in contact with the fluid.

When fluids are characterized, usually the sensor responses in the presence and in the absence of the fluid are compared. Therefore it is very important that the reference (sensor response in the absence of the fluid) does not change during the measurements. In particular, the sensor response depends on the temperature of the sensor. The method outlined above can be used to determine the sensor temperature during the measurement of the fluid. While the fluid temperature and the sensor temperature are somewhat correlated, they are not necessarily the same.

Figure 10:
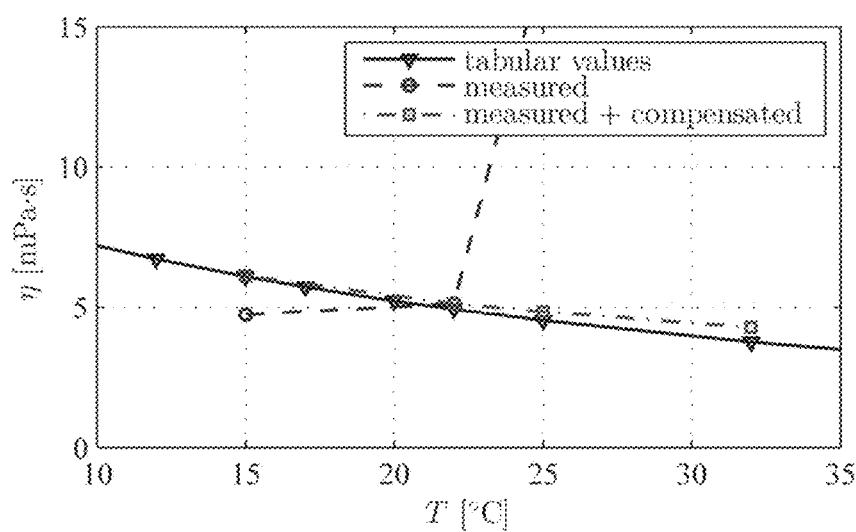
FIG. 10 is a diagram showing viscosity determinations by measuring the resonance frequency shift with and without temperature compensation.

This method is particularly interesting if viscosity is not determined via measuring the damping, but via measuring the resonance frequency. This is illustrated in FIG. 10, which shows viscosity determinations by measuring the resonance frequency shift with and without temperature compensation. Temperature was determined by observing the first mode at around 2590 Hz, while viscosity was determined by measuring the frequency shift of the second mode at around 5590 Hz. Without temperature compensation, a determination of viscosity via measuring the resonance frequency is virtually impossible.

The invention claimed is:

1. A method to measure the vibrational characteristics of an oscillating system using a control system, said oscillating system comprising a resonator, at least one vibration exciter and at least one sensor, the method comprising:

exciting said resonator by said at least one vibration exciter, measuring a motion of said resonator by said at least one sensor, operating said control system to control said motion of said resonator by said at least one vibration exciter, based on sensor output received from said at least one sensor, wherein said motion of said resonator is a superposition of at least two harmonic motions, wherein said control system comprises at least two subcontrollers, wherein each of said at least two harmonic motions is controlled independently by one of said at least two subcontrollers, said at least two harmonic motions being controlled by said at least two subcontrollers simultaneously.

2. The method according to claim 1, wherein said at least two subcontrollers are phase-locked loops.

3. The method according to claim 1, wherein each of said at least two harmonic motions has a frequency close to a resonance frequency of said resonator.

4. The method according to claim 1, wherein resonance frequencies of said resonator are sensitive to properties of a fluid, being in contact with said resonator.

5. The method according to claim 4, wherein said fluid properties are the density and viscosity of said fluid.

6. The method according to claim 4, wherein said fluid properties are viscoelastic properties of said fluid.

7. The method according to claim 1, wherein the resonator is a tube-like structure and said resonator's resonance frequencies are sensitive to the mass flow of a fluid through said tube-like structure.

8. The method according to claim 1, wherein a single transducer acts as the at least one vibration exciter and the at least one sensor.

9. The method according to claim 2, wherein at least one of said phase-locked loops is a gated phase-locked loop containing at least one switch.

10. The method according to claim 1, wherein some or all of said at least two subcontrollers have individual inputs connected to form a common input and have individual outputs which are connected to an adder having a common output, and wherein the common input and/or the common output are gated by switches.

11. The method according to claim 1, wherein said at least two subcontrollers are used with two different reference phase settings to measure the damping of the resonator.

12. The method according to claim 1, wherein said at least two subcontrollers are used to measure amplitudes of said at least two harmonic motions.

13. A device comprising an oscillating system and a control system, said oscillating system comprising a resonator, at least one vibration exciter and at least one sensor, the resonator being coupled to the at least one vibration exciter for exciting a motion of the resonator, the at least one sensor being configured to measure said motion of the resonator, the control system being configured to control the motion of the resonator via the at least one vibration exciter, based on sensor output received from the at least one sensor, wherein the motion of the resonator is a superposition of at least two harmonic motions, the control system comprising at least two subcontrollers, each of said at least two subcontrollers being configured to independently control one of said at least two harmonic motions, the at least two subcontrollers being configured to control said at least two harmonic motions simultaneously.

14. The device according to claim 13, wherein each of said at least two subcontrollers comprises a phase-locked loop.

15. The device according to claim 13, wherein each of said at least two subcontrollers is configured to control a harmonic motion that has a frequency close to a resonance frequency of said resonator.

16. The device according to claim 13, wherein said resonator has a plurality of resonance frequencies, said resonance frequencies being sensitive to properties of a fluid that is in contact with said resonator.

17. The device according to claim 16, wherein said fluid properties are density and viscosity of said fluid.

18. The device according to claim 16, wherein said fluid properties are viscoelastic properties of said fluid.

19. The device according to claim 16, wherein the resonator is a tube-like structure, and said resonance frequencies are sensitive to a mass flow of a fluid through said tube-like structure.

20. The device according to claim 13, wherein a single transducer acts as the at least one vibration exciter and the at least one sensor.

21. The device according to claim 14, at least one of said phase-locked loops is a gated phase-locked loop containing at least one switch.

22. The device according to claim 13, wherein some or all of said at least two subcontrollers have individual inputs connected to form a common input and have individual outputs, wherein the device comprises an adder having inputs that are connected to the individual outputs of said at least two subcontrollers and having a common output, and wherein the device comprises one or more switches for gating the common input and/or the common output.

23. The device according to claim 13, where said at least two subcontrollers are configured to operate with two different reference phase settings to measure the damping of the resonator.

24. The device according to claim 13, where said at least two subcontrollers are configured to measure amplitudes of said at least two harmonic motions.

* * * * *